United States Patent [19]
Kethley

[11] 3,937,063
[45] Feb. 10, 1976

[54] VAPOR PRESSURE METERING APPARATUS AND METHOD

[76] Inventor: Lancelot I. Kethley, 1454 36th Ave. Apt. 6, Oakland, Calif. 94601

[22] Filed: June 28, 1974

[21] Appl. No.: 484,128

Related U.S. Application Data

[63] Continuation-in-part of Ser. No. 369,838, June 14, 1973, abandoned.

[52] U.S. Cl. .......................... 73/29; 73/335; 73/337
[51] Int. Cl.² ............................................. G01W 1/06
[58] Field of Search ......... 73/29, 335, 337.5, 338.3, 73/64.2, 337

[56] References Cited
UNITED STATES PATENTS

| | | | |
|---|---|---|---|
| 2,255,734 | 9/1941 | McGrath | 73/338.3 |
| 2,866,339 | 12/1958 | Rhodes | 73/64.2 |
| 3,459,034 | 8/1969 | Kawaguchi | 73/29 |

FOREIGN PATENTS OR APPLICATIONS

| | | | |
|---|---|---|---|
| 525,896 | 2/1954 | Belgium | 73/29 |

*Primary Examiner*—S. Clement Swisher
*Assistant Examiner*—Denis E. Corr
*Attorney, Agent, or Firm*—Theodore J. Bielen, Jr.; Richard Esty Peterson

[57] ABSTRACT

An apparatus and method for continuously metering the vapor pressure of a gaseous component of a material within a gaseous mixture utilizing a saturation vapor pressure sensor having a linear dimension changeable with respect to changes in the saturation vapor pressure of the material, a relative humidity sensor having a linear dimension changeable with respect to changes in the relative humidity of said gaseous mixture, and a means to contrast the linear dimension of one of said sensors to the linear dimension of the other, the resultant value representing the vapor pressure of said material.

9 Claims, 4 Drawing Figures

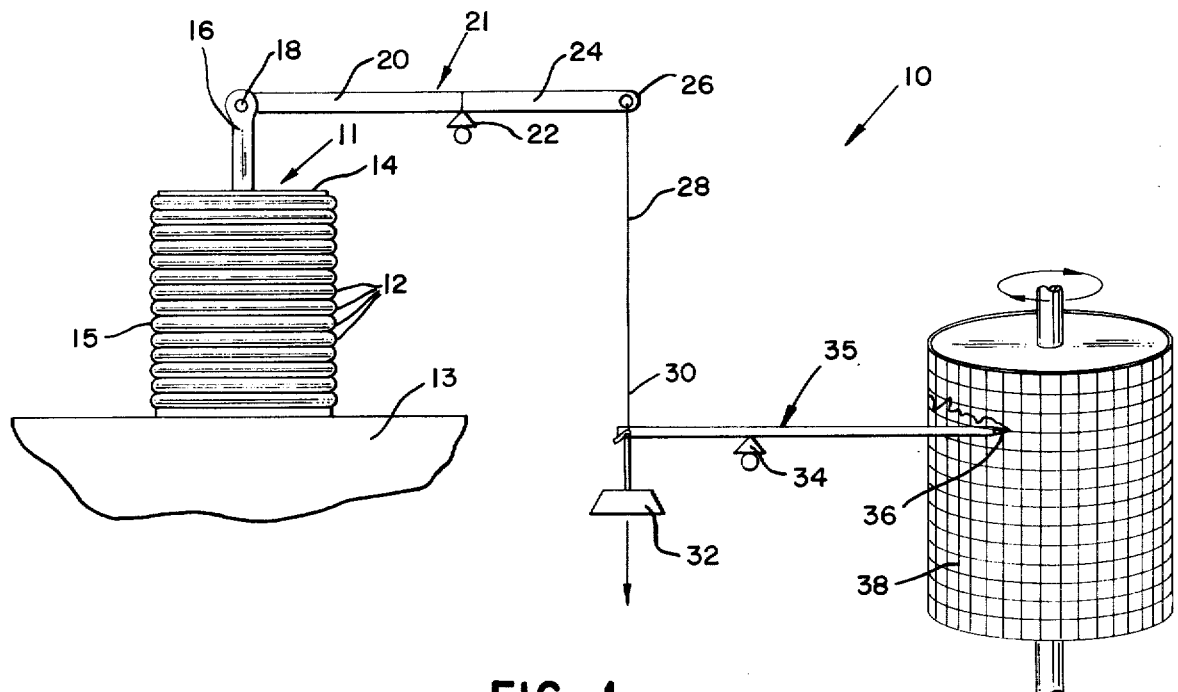
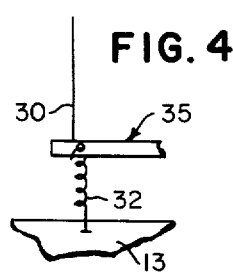
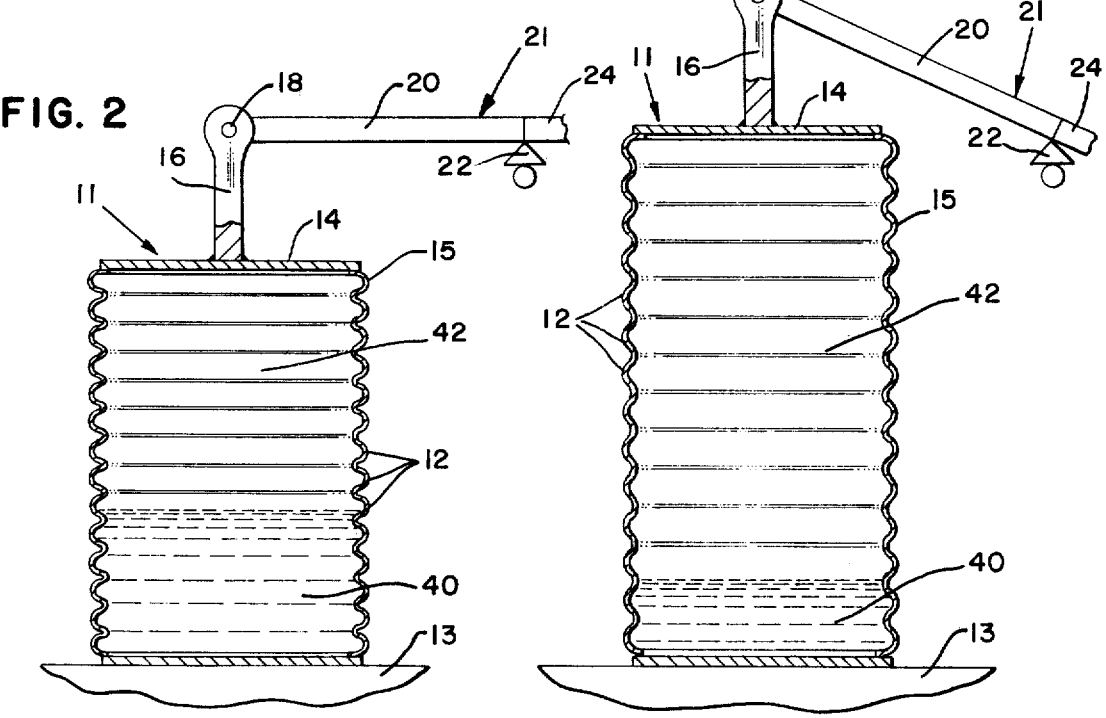

VAPOR PRESSURE METERING APPARATUS AND METHOD

CROSS-REFERENCE TO RELATED APPLICATION

The present application is a continuation-in-part of applicant's application, Ser. No. 369,838, filed June 14, 1973 now abandoned.

BACKGROUND OF THE INVENTION

This invention relates to a novel apparatus and method for measuring the vapor pressure (sometimes called partial pressure) of a material in a gaseous mixture. The apparatus is particularly useful, although not limited to, detecting the vapor pressure of water in air, the value of which may be used to ascertain the absolute humidity, specific humidity, dew point temperature, and the like.

With reference to meteorological observation and data gathering, there has been a need for an instrument allowing measurement of the vapor pressure of water in the atmosphere to aid in meteorological studies. For instance, evaluation of evaporation intensity of a body of water, prediction of cloud level, frost occurrence, and the like is predicted upon an accurate measurement of the vapor pressure of water in its gaseous phase.

As is known in the art, relative humidity, being a ratio, does not allow reckoning of the vapor pressure without knowledge of other factors. Previous methods of gaging the vapor pressure of a material have been difficult to use and expensive to manufacture. For example, the psychrometric apparatus presents difficulty in that it requires a continuous supply of the liquid phase of the metered material and diagrams, tables, or the like to evaluate the vapor pressure. The fogging-mirror type of instrument necessitates an electrical source of energy, as well as expensive electronic components.

SUMMARY OF THE INVENTION

The present invention is a method and apparatus for the accurate measurement of the vapor pressure of a gaseous material within a gaseous mixture. The apparatus includes a saturation vapor pressure sensor formed by a closed container, such as a bourdon tube, capsule, cell, or the like. A predetermined amount of the material being metered is disposed within the closed container such that the material exists in the vapor state over the liquid or solid state at all times. In addition, the container must flex so that increasing saturation vapor pressure increases the linear dimension of the container. A linearly changeable relative humidity sensor, such as a hygroscopic thread, combines with the saturation vapor pressure sensor through a means to contrast the change in length of one sensor from the change in length of the other sensor.

For example, in the preferred embodiment, the end of the closed container imparts its linear expansions or contractions to one arm of a lever. The other arm of the lever affixes to the relative humidity sensor. The linking of the saturation vapor pressure sensor and the relative humidity sensor permits the gaging of the vapor pressure of the material simply by measuring the change in position of the end of the relative humidity sensor; i.e., the end connected to the indicator.

A recording chart, indicator, read out, or the like may be employed to convey the vapor pressure. Since related information, such as dew point temperature, specific humidity, and the like are readily ascertainable via mathematical or graphical methods, the chart can be scaled accordingly.

Therefore, it is an object of the present invention to provide a simple and accurate apparatus and method for the measurement of the vapor pessure or partial pressure of a material in a gaseous mixture.

Likewise, it is a further object of the present invention to provide a useful tool for the measuring and gathering of useful meteorological data.

A further aspect of the present invention is to determine the vapor pressure of a material employing the known parameters of saturation vapor pressure and relative humidity.

Yet another objective is to provide information inferred from the vapor pressure of a component of a gaseous mixture accurately and quickly.

The invention possesses other objects and advantages, especially as concerns particular features and characteristics thereof, which will become apparent as the specification continues.

BRIEF DESCRIPTION OF THE DRAWINGS

FIG. 1 is a schematic view of the apparatus.

FIG. 2 is a broken sectional view depicting the saturation vapor pressure sensor.

FIG. 3 is a broken sectional view of the saturation vapor pressure sensor in a relatively expanded state.

FIG. 4 is an elevational view of alternate tension means.

DESCRIPTION OF THE PREFERRED EMBODIMENTS

The apparatus is depicted in its entirety by the numeral 10 and, in FIG. 1, includes a saturation vapor pressure sensor 11, including a flexible corrugated container 15 set on a surface 13. The upper end of the container 15 is provided with a plate 14, which serves to enclose the container 15 and to impart linear expansion or contraction of the container to leg 16. The closed container may take the form of a bourdon tube or capsule, but, in any case, the container changes its linear dimension with respect to the change of the saturation vapor pressure of the material being metered.

Vapor pressure of the metered material is defined as the partial pressure of the gaseous phase of the metered material in a gaseous mixture. Saturation vapor pressure is defined as the vapor pressure of the vapor phase of the metered material in contact with its liquid form.

As shown by FIG. 2, the container 15 is constructed with flexible corrugations 12, which gives it the characteristic of linear variation of the long axis of the container with changing saturation vapor pressure. The liquid component 40 of the material being metered partially fills the container 15. A vapor space 42 necessarily contains the saturation vapor phase of the material in a mixture with other gases of a predetermined environment. In the case of the earth's atmosphere, the vapor space 42 incorporates oxygen, nitrogen, argon, carbon dioxide, and any other gases found in the atmosphere in the proper proportions. If the material being metered is water vapor, then the vapor space 42 will always be saturated with water vapor.

The saturation vapor pressure sensor 11 changes its length in proportion to the saturation vapor pressure of the material being metered according to the following mathematical relationship:
$$\Delta l_p = c\Delta P_s$$
where $\Delta l_p$ is the change in length of the container 15, $c$ is a dilatational constant determined by the composition of the container, and $\Delta P_s$ is the change in saturation vapor pressure of the material being metered.

The saturation vapor pressure increases pursuant to the following:
$$P_s = 10^{B-A/T}$$
where $P_s$ is the saturation vapor pressure of the metered material, $A$ and $B$ are constants of the gaseous phase of the metered material, values of which can be calculated, for example, from the Smithsonian Vapor Pressure Tables, and $T$ represents the absolute temperature of the gaseous mixture.

When the temperature of the system 10 rises, a portion of the liquid phase 40 evaporates into the vapor space 42 to maintain the condition of saturation by the vapor phase of the metered material. Therefore, container 15, by dint of its flexible corrugations 12, will expand linearly, within reasonable limits, and push lever arm 20 upwardly according to the value of the saturation vapor pressure of the metered material.

The relatively rigid plate 14 on the upper portion of closed container 15, as aforesaid, moves linearly with the expansion and contraction of the container. Leg 16 affixes to plate 14 on one end and pivotally attaches to lever arm 20 on the other end through pivot pin 18. Leg 16 is preferably mounted substantially perpendicular to lever arm 20, horizontally disposed and aligned with the long axis of container 15, as depicted in FIG. 1. However, leg 16 may be mounted in angular relationship with lever arm 20 as long as there exists a vertical component of the force of leg 16 upon the lever arm.

Fulcrum 22 supports the lever 21, which includes lever arms 20 and 24. Lever arm 24 is constructed of a different material than lever arm 20 for reasons as will be discussed below. Attached to opening 26 is the relative humidity sensor 28 which comprises a hygroscopic thread or the like. As is well known in the art, a hygroscopic thread changes linear dimension as a consequence of relative humidity. The lower end of the humidity sensor attaches to a counterweight or spring 32 FIG. 4 and an end of lever 35 having a fulcrum 34.

The relative humidity sensor 28 changes its length in relation to the relative humidity of the metered material within the gaseous mixture in intimate contact with the sensor 28. Consequently, the following is true of the relative humidity sensor:
$$\Delta l_h = k\Delta R$$
where $\Delta l_h$ is the change in length of the relative humidity sensor, $k$ is a proportionality constant pertaining to the characteristic of the material composing the hygroscopic thread, and $R$ is the relative humidity of the gaseous mixture in intimate contact with the sensor 28. Accordingly:
$$R = (P_e/P_s)\,100$$
where $P_e$ is the vapor pressure of the metered material and $P_s$ is the saturation vapor pressure of the metered material.

A pen 36 on the end of lever 35 opposite the end attached to the relative humidity sensor 28 records the movement of the lower end 30 of the relative humidity sensor 28. This takes place on a strip or drum chart recorder 38 or the like, as is well known in the art.

In operation with the instrument properly calibrated, an increase in the saturation vapor pressure of the metered material will expand container 15 which, in turn, pushes lever arm 20 upwardly through plate 14 and leg 16 and vice versa. Simultaneously, a decrease in the relative humidity will shorten the length of the relative humidity sensor 28 and vice versa. The combined effect of the relative humidity sensor and the saturation vapor pressure sensor is recorded on the drum chart 38.

For example, when the temperature of the environment increases with a constant vapor pressure of the metered material, the saturation vapor pressure of the metered material increases, which causes lever arm 20 to move upwardly and arm 24 to move downwardly. At the same time, the relative humidity sensor 28 contracts. The combined effect to both sensors will keep the pen 36 steady, indicating no change in the vapor pressure, $P_e$, of the material metered. In other words:
$$\Delta l_p + \Delta l_h = 0$$
with a change in temperature of the system 10.

Counterweight or spring 32 serves to provide sufficient tension on sensor 28 to maintain it in a straight configuration.

As heretofore discussed, the material whose vapor pressure is most commonly measured is water in the earth's atmosphere. But sensors may be used to measure the vapor pressure of other materials such as ether, ammonia, and the like in other gaseous mixtures.

The vapor pressure $P_e$ may be continuously recorded in any pressure units, such as millibars, millimeters of mercury, pounds per square inch, and the like. Dew point temperature, specific humidity, and absolute humidity may be graphically or mathematically found from the value of the vapor pressure. Likewise, the drum chart recorder 38 may directly indicate any of these values, as desired.

To aid in calibration of the system 10, arm 24 may be constructed of material with a desired coefficient of thermal expansion and length to compensate for the exponential variation of saturation in the vapor pressure sensor and the linear variation of the relative humidity sensor, as discussed above.

The foregoing description may be seen to include a method of measuring the vapor pressure of a gas. The method incorporates the steps of measuring the linear displacement of saturation vapor pressure sensor 15, measuring the length of the relative humidity sensor 28. The lengths of both are contrasted by the use of levers 21 and 35 to determine the value of the vapor pressure.

It should be noted that one skilled in the art may further compensate the apparatus 10 for changes in barometric pressure by raising or lowering surface 13. For instance, an increase in barometric pressure will cause plate 14 to move downwardly; therefore, surface 13 must move upwardly a corresponding distance.

While in the foregoing specification embodiments of the invention has been set forth in considerable detail for the purpose of making a complete disclosure thereof, it will be apparent to those skilled in the art that numerous changes may be made in such details without departing from the spirit and principles of the invention.

What is claimed is:

1. A device for continuously measuring the vapor pressure of the vapor phase of a material within a gaseous mixture comprising:
   a. saturation vapor pressure sensor including a closed container of at least two phases of the material, one of which is the vapor phase in the predetermined gaseous mixture, a linear dimension of said container being changeable with respect to changes in the saturation vapor pressure of the material;
b. relative humidity sensor within the predetermined gaseous mixture, a linear dimension of said sensor changeable with respect to changes in the relative humidity of said gaseous mixture; and
c. means to contrast the linear dimension of one of said sensors to the linear dimension of said other sensor, the resultant value representing the vapor pressure of the material.

2. The device of claim 1 in which said means to contrast the linear dimensions includes a first lever having a first and second arm, the first arm of which affixes to said saturation vapor pressure sensor such that a force component of said change in linear dimension of said saturation vapor pressure sensor acts substantially perpendicularly to said first arm, said relative humidity sensor having a first end portion and a second end portion along said changeable linear dimension, said second arm affixing to said first end portion of said relative humidity sensor, and means to measure the position of said second end portion of said relative humidity sensor.

3. The device of claim 2 in which said means to measure the position of said second end portion of said relative humidity sensor includes a second lever having a first arm and a second arm, said first arm attached to said second end portion of said relative humidity sensor and said second arm including a marker to indicate the position of said second arm.

4. The device of claim 3 in which said relative humidity sensor includes a hygroscopic thread and means to furnish tension to said thread.

5. The device of claim 4 in which said means to furnish tension to said thread comprises a counterweight affixed to the connection of said first arm of said second lever and said second end portion of said relative humidity sensor.

6. The device of claim 4 in which said means to furnish tension to said thread comprises a spring affixed to the connection of said first arm of said second lever and said second end portion of said relative humidity sensor.

7. The device of claim 3 which additionally comprises a means to indicate the position of said second arm of said second lever.

8. The device of claim 7 in which said second arm of said first lever changes the linear dimension of said relative humidity sensor with respect to changes in temperature of said gaseous mixture so as to properly calibrate said device.

9. A method of continuously measuring the vapor pressure of the vapor phase of a material within a gaseous mixture comprising the steps of:
a. translating the saturation vapor pressure of the material into a linear dimension;
b. translating the relative humidity of the material into a linear dimension; and
c. contrasting said linear dimensions, the resultant value representing the vapor pressure of the material.

* * * * *